United States Patent [19]

Degnan et al.

[11] Patent Number: 5,601,699
[45] Date of Patent: Feb. 11, 1997

[54] METHOD FOR CRACKING HYDROCARBONS

[75] Inventors: Thomas F. Degnan, Moorestown, N.J.; Terry E. Helton, Glen Mills, Pa.; Grant H. Yokomizo, Edison, N.J.

[73] Assignee: Mobil Oil Corporation, Fairfax, Va.

[21] Appl. No.: 444,978

[22] Filed: May 19, 1995

Related U.S. Application Data

[62] Division of Ser. No. 245,275, May 18, 1994, Pat. No. 5,472,922.

[51] Int. Cl.[6] .................................................. C10G 11/02
[52] U.S. Cl. ........................ 208/114; 208/113; 208/118; 208/120; 208/121; 208/122
[58] Field of Search ............................ 208/113, 114, 208/118, 120, 121, 122

[56] References Cited

U.S. PATENT DOCUMENTS

| | | | |
|---|---|---|---|
| 3,972,832 | 8/1976 | Butter et al. | 252/437 |
| 4,567,152 | 1/1986 | Pine | 502/64 |
| 4,584,091 | 4/1986 | Pine | 208/114 |
| 4,724,066 | 2/1988 | Kirker et al. | 208/114 |
| 4,873,211 | 10/1989 | Walker et al. | 502/64 |
| 5,110,776 | 5/1992 | Chitnis et al. | 502/64 |
| 5,126,298 | 6/1992 | Absil et al. | 502/68 |
| 5,190,902 | 3/1993 | Demmel | 502/63 |
| 5,194,412 | 3/1993 | Roberie et al. | 502/64 |
| 5,231,064 | 7/1993 | Absil et al. | 502/68 |
| 5,232,579 | 8/1993 | Absil et al. | 208/113 |

Primary Examiner—Michael Lewis
Assistant Examiner—Thomas G. Dunn, Jr.
Attorney, Agent, or Firm—G. L. Harris

[57] ABSTRACT

Methods for preparing phosphorus containing catalysts comprising a large-pore zeolite, e.g., zeolite Beta, zeolite ZSM-12, or zeolite ZSM-20, and a matrix which have improved attrition resistance. The present invention includes the catalyst compositions produced by the above methods. Also included in the present invention are methods for the use of catalysts prepared by the present method in hydrocarbon cracking processes. It is desired to develop cracking catalysts for organic compound conversion that have improved cracking yields and have good attrition resistance. This invention involves the use of large pore siliceous zeolites and a highly siliceous matrix to produce a cracking catalyst with improved cracking yields and good attrition resistance. The invention further involves the use of phosphorus and the use of selected sequences for combining the compounds in the manufacture of the catalyst to enhance the attrition resistance of the catalyst.

18 Claims, No Drawings

METHOD FOR CRACKING HYDROCARBONS

CROSS-REFERENCE TO RELATED APPLICATIONS

This is a division of application Ser. No. 08/245,275, now U.S. Pat. No. 5,472,922 filed on May 18, 1994.

BACKGROUND OF THE INVENTION

This invention relates to a new and useful method for manufacturing a catalyst composition comprising a large-pore siliceous crystalline molecular sieve, phosphorus, and a matrix material, the new catalyst composition, and use of the new catalyst composition in accordance herewith as a catalyst component for organic compound, e.g., hydrocarbon compound, conversion.

More particularly, this invention relates to a method for preparing a catalyst composition comprising large-pore siliceous crystals, for example, those having the structure of zeolite Beta, ZSM-12, or ZSM-20, wherein the catalyst composition is manufactured in a special way to impart thereto certain valuable catalytic and physical properties and handling characteristics. This invention also relates to the catalyst itself and the use of the catalyst in organic compound conversion.

Catalysts used in Fluid Catalytic Cracking (FCC) processes should be resistant to mechanical attrition, that is, the formation of fines which are small particles, e.g., less than 20 microns in size. The cycles of cracking and regeneration at high flow rates and temperature, such as in an FCC process, have a tendency to break down the catalyst into smaller particles, called "fines," which have a diameter of up to 20 microns as compared with an average diameter of catalyst particles of about 60–100 microns. In an FCC process, catalyst particles typically range from about 10 to about 200 microns, for example, from about 20 to about 150 microns. Excessive generation of catalyst fines increases the refiner's catalyst cost and can be undesirable from an environmental standpoint. It is desirable to develop a catalyst useful in a FCC process that is resistant to mechanical attrition.

Large-pore siliceous crystalline materials include, for example, zeolites having the structure of Beta, ZSM-12, or ZSM-20. Zeolite Beta and its preparation are taught in U.S. Pat. No. 3,308,069, incorporated entirely herein by reference. ZSM-12 and its preparation are taught in U.S. Pat. Nos. 3,832,449 and 4,552,739, incorporated entirely herein by reference. ZSM-20 and a method for its preparation are taught in U.S. Pat. No. 3,972,983, incorporated entirely herein by reference.

U.S. Pat. No. 4,642,226 teaches a method for synthesizing crystals having the structure of zeolite Beta from a reaction mixture comprising dibenzyldimethylammonium ions as directing agent, and the crystals synthesized thereby. U.S. Pat. No. 5,164,170 discloses a method for synthesizing large crystal size zeolite Beta from a reaction mixture using a directing agent comprising tetraethylammonium compound and including triethanolamine, and the crystals synthesized thereby.

U.S. Pat. No. 4,391,785 teaches a method for synthesis of zeolite ZSM-12 from a reaction mixture comprising, as a directing agent, a compound selected from the group consisting of dimethylpyridinium halide and dimethyl pyrrolidinium halide.

U.S. Pat. No. 4,112,056 teaches a synthesis method for ZSM-12 from a reaction mixture containing tetraethylammonium ions as directing agent. U.S. Pat. No. 4,452,769 claims a method for synthesizing ZSM-12 from a reaction mixture containing methyltriethylammonium ions as the directing agent. European Patent Application 13,630 claims synthesis of ZSM-12 from a reaction mixture containing a directing agent defined as an organic compound containing nitrogen and comprising "an alkyl or aryl group having between 1 and 7 carbon atoms, at least one of which comprises an ethyl radical." U.S. Pat. No. 4,482,531 teaches synthesis of ZSM-12 with a DABCO-$C_n$-diquat, n being 4, 5, 6, or 10, directing agent; and U.S. Pat. No. 4,539,193 teaches use of bis(dimethylpiperidinium) trimethylene directing agent for synthesis of ZSM-12.

U.S. Pat. No. 4,021,141 teaches synthesis of the ZSM-12 structure from a reaction mixture comprising hexamethyleneimine directing agent.

The entire contents of the above disclosures are incorporated herein by reference as to synthesis and description of the zeolite Beta and ZSM-12 structures and synthesis.

Cracking catalysts for use in petroleum processing generally consist of a zeolitic component and a matrix. The zeolitic material is generally dispersed in an inorganic oxide-type sol or gel matrix material to which one or more clays are added.

Because of the need for higher octane gasoline, there has been an emphasis on octane-increasing improvements in cracking catalysts. Octane-enhancing zeolitic fluid cracking catalysts have been reviewed recently by Scherzer, *Catal. Rev. Sci. Eng.*, 31 (3), 215–354 (1989). The matrix components described in the article include natural or modified clays and inorganic oxides such as silica, alumina, silica-alumina, and silica-magnesia. Other inorganic oxides described for matrices are $TiO_2$, $ZrO_2$, $P_2O_5$, and $B_2O_3$.

Cracking catalysts comprising a zeolite and a matrix material containing aluminum phosphate have been described, for example, in U.S. Pat. Nos. 4,873,211 and 4,228,036. Such catalysts comprising a zeolite and an inorganic oxide matrix which contains phosphorus-treated alumina particles are described in U.S. Pat. Nos. 4,567,152 and 4,584,091 along with U.S. Pat. No. 5,194,412 and in European Patent Applications 176,150 and 403,141. The treatment of zeolite catalysts with phosphoric acid to provide a phosphorus-containing catalyst is described in U.S. Pat. Nos. 4,839,319 and 4,498,975.

In U.S. Pat. No. 4,430,199, tricresyl or ammonium hydrogen phosphate is impregnated into a cracking catalyst to improve the tolerance toward poisoning metals. In addition, boron may be added as a passivating agent.

SUMMARY OF THE INVENTION

An economical and reproducible method is provided for preparing an improved catalyst composition comprising siliceous crystals having large pores, i.e., pores having effective cross-sectional diameters of about 7 Angstroms or more, examples of which include crystals having the structure of zeolite Beta, ZSM-12, or ZSM-20, exhibiting valuable catalytic activity and selectivity and other valuable properties. The method comprises a first step of combining the appropriate large pore highly siliceous crystalline material, e.g., zeolite of the Beta, ZSM-12, or ZSM-20 structure; source of silica; clay; source of phosphorus; and, if desired, source of alumina. The second step of the method comprises forming catalyst particles from the product of the first step.

The second step product catalyst material may then be calcined at a temperature of from about 200° C. to about 550° C. for from about 1 minute to about 48 hours. Following conversion of the catalyst to the active (i.e., hydrogen) form by, for example, ammonium exchange and calcination, the calcined catalyst will have an alpha value of greater than about 10, usually from greater than about 20 to about 300. A calcination procedure in accordance herewith would be to provide a calcined product catalyst which retains a trace amount of carbon residue. Therefore, partial calcination within the above conditions, e.g., at lower temperature and/or shorter time, may be done.

The composition of the first step combination must comprise a binder alumina/phosphorus weight ratio of less than about 5, preferably less than about 2. Further, the binder alumina to phosphorus ratio should be less than about 10 for the catalyst product of calcination. "Binder alumina" is alumina from sources other than the siliceous crystalline material, e.g., zeolite Beta. Further, the binder silica to alumina ratio should be greater than about 5. "Binder silica" is silica from sources other than the crystalline material, e.g., zeolite Beta.

Unexpectedly, the sequence in which the components are combined has been found to influence the attrition resistance of the catalyst composition. One sequence for combining the components into the mixture of the first step that is effective in this invention includes first forming a slurry of a source of silica (S) and a source of alumina (A), then adding the siliceous crystalline material (Z), then adding clay (C), and finally adding a source of phosphorus (P). This sequence may be represented in a short-hand fashion as SAZCP. Short-hand representations for other sequences that are also effective in this invention include CPZSA, SCZPA, SAZPC, SAPZC, APZSC and, where no alumina is added, SCZP. The order of combining the first two components is not important, e.g., SAZPC is equivalent to ASZPC. An additional improvement in attrition resistance has been achieved as a part of this invention by aging the mixture before spray drying.

DETAILED DESCRIPTION OF THE INVENTION

The invention is a new and useful method for manufacturing a catalyst composition comprising a large-pore siliceous crystalline molecular sieve, phosphorus, and a matrix material, the new catalyst composition, and use of the new catalyst composition in accordance herewith as a catalyst component for organic compound, e.g., hydrocarbon compound conversion.

More particularly, this invention relates to a method for manufacture of an improved catalyst composition comprising a first step of forming a slurry by combining a siliceous crystalline material having the structure of zeolite Beta, zeolite ZSM-12, or zeolite ZSM-20, with a binder comprising a source of phosphorous and at least two compounds selected from a source of silica, clay, and optionally, a source of alumina, in a mixer under aqueous conditions and a second step of spray drying the mixture at a pH less than or equal to about 5.

The spray dried catalyst composition may then be calcined at a temperature of from about 200° C. to about 550° C. for from about 1 minute to about 48 hours. Following conversion of the catalyst to the active (i.e. hydrogen) form by, for example, ammonium exchange and calcination, the calcined catalyst will have an alpha value of greater than about 10, usually from greater than about 20 to about 300. A calcination procedure in accordance herewith would be to provide a calcined product catalyst which retains a trace amount of carbon residue. Therefore, partial calcination within the above conditions, e.g., at lower temperature and/or shorter time, may be done.

Both the integrity of the catalyst (i.e. attrition resistance) and the performance of the catalyst may be improved with the binder alumina to phosphorus weight ratio is less than about 5 and preferably less than about 2. Also, the binder alumina to phosphorus weight ratio in the calcined catalyst product should be less than about 10. "Binder alumina" is alumina from sources other than the siliceous crystalline material, e.g., zeolite Beta. Further, the binder silica to alumina ratio should be greater than about 5. "Binder silica" is silica from sources other than the siliceous crystalline material, e.g., zeolite Beta.

The pH of the mixture to be spray dried should between about 1 and about 5. The mixture may be aged before spray drying, e.g., generally, the mixture may be aged for about 1 hour to about 24 hours before spray drying, specifically about 4 hours to about 12 hours.

In a typical embodiment, the catalyst composition contains the following components in the designated weight percent ranges:

|  | Weight Percent |
| --- | --- |
| Zeolite | 2 to about 60 |
| Silica | 10 to about 80 |
| Clay | 5 to about 70 |
| Phosphorous | 0.5 to about 10 |
| Alumina | 0 to about 22 |

Unexpectedly, the sequence in which the components are combined has been found to influence the attrition resistance of the catalyst composition. One sequence for combining the components into the mixture of the first step that is effective in this invention includes forming a slurry of a source of silica (S) and a source of alumina (A), then adding the siliceous crystalline material (Z), e.g., zeolite Beta, zeolite ZSM-12, or ZSM-20, then adding clay (C), and finally adding a source of phosphorus (P). This sequence may be represented in a short-hand fashion as SAZCP. Short-hand representations for other sequences that are also effective in this invention include CPZSA, SCZPA, SAZPC, SAPZC, APZSC and, where no alumina is added, SCZP. The order of combining the first two components is not important, e.g., SAZPC is equivalent to ASZPC.

In the practice of this invention, the source of silica may comprise a compound selected from colloidal silica, sodium silicate, polysilicic acid, ammonium polysilicate solution, silica sol, silica gel and mixtures thereof. The source of alumina may comprise a compound selected from pseudoboehmite, aluminum salts and mixtures thereof. Clays useful in the present invention comprise clays selected from kaolin, metakaolin, smectite and mixtures thereof. The source of phosphorous useful in the present invention comprises a phosphorous containing compound selected from ammonium monohydrogen phosphate, ammonium dihydrogen phosphate, triammonium phosphate, ammonium hypophosphate, ammonium orthophosphate, ammonium dihydrogen orthophosphate, ammonium monohydrogen orthophosphate, ammonium hypophosphite, ammonium dihydrogen orthophosphite, phosphoric acid and mixtures thereof.

The catalyst composition of this invention is useful as a catalyst for organic compound, e.g., hydrocarbon compound, conversion. Non-limiting examples of processes for organic compound conversion include Fluid Catalytic Cracking (FCC) and other forms of catalytic cracking including moving bed catalytic cracking and hydrocracking. Suitable catalytic cracking conditions include a temperature ranging from about 700° F. to about 1300° F. and a pressure ranging from subatmospheric to several hundreds of atmospheres.

The catalytic process can be either fixed bed, moving bed, transfer line, or fluidized bed, and the hydrocarbon flow may be either concurrent or countercurrent to the catalyst flow. The process of the invention is particularly applicable to the Fluid Catalytic Cracking (FCC) or Thermofor Catalytic Cracking (TCC) processes. In both of these processes, the hydrocarbon feed and catalyst are passed through a reactor and the catalyst is regenerated. The two processes differ substantially in the size of the catalyst particles and in the engineering contact and transfer which is at least partially a function of catalyst size.

The TCC process is a moving bed and the catalyst is in the shape of pellets or beads having an average particle size of about one-sixty-fourth to one-fourth inch. Active, hot catalyst beads progress downwardly cocurrent with a hydrocarbon charge stock through a cracking reaction zone. The hydrocarbon products are separated from the coked catalyst and recovered, and the catalyst is recovered at the lower end of the zone and regenerated.

Typical TCC conversion conditions include an average reactor temperature of from about 450° C. to about 540° C.; catalyst/oil volume ratio of from about 2 to about 7; reactor volume hourly space velocity of from about 1 to about 5 vol./hr./vol.; and recycle to fresh feed ratio of from 0 to about 0.5 (volume).

The process of the invention is also applicable to Fluid Catalytic Cracking. In fluidized catalytic cracking processes, the catalyst is a fine powder of about 10 to 200 microns. This powder is generally suspended in the feed and propelled upward in a reaction zone. A relatively heavy hydrocarbon feedstock, e.g., a gas oil, is admixed with a suitable cracking catalyst to provide a fluidized suspension and cracked in an elongated reactor, or riser, at elevated temperatures to provide a mixture of lighter hydrocarbon products. The gaseous reaction products and spent catalyst are discharged from the riser into a separator, e.g., a cyclone unit, located within the upper section of an enclosed stripping vessel, or stripper, with the reaction products being conveyed to a product recovery zone and the spent catalyst entering a dense catalyst bed within the lower section of the stripper. In order to remove entrained hydrocarbons from the spent catalyst prior to conveying the latter to a catalyst regenerator unit, an inert stripping gas, e.g., steam, is passed through the catalyst bed where it desorbs such hydrocarbons conveying them to the product recovery zone. The fluidizable catalyst is continuously circulated between the riser and the regenerator and serves to transfer heat from the latter to the former thereby supplying the thermal needs of the cracking reaction which is endothermic.

The FCC conversion conditions include a riser top temperature of from about 500° C. to about 595° C., specifically from about 520° C. to about 565° C., and most specifically from about 530° C. to about 550° C.; catalyst/oil weight ratio of from about 3 to about 12, specifically from about 4 to about 11, and most specifically from about 5 to about 10; and catalyst residence time of from about 0.5 to about 15 seconds, specifically from about 1 to about 10 seconds.

It is generally necessary that the catalysts be resistant to mechanical attrition, that is, the formation of fines which are small particles, e.g., less than 20 µm. The cycles of cracking and regeneration at high flow rates and temperatures, such as in an FCC process, have a tendency to break down the catalyst into fines, as compared with an average diameter of catalyst particles of about 60–100 microns. In an FCC process, catalyst particles range from about 10 to about 200 microns, preferably from about 20 to 150 microns. Excessive generation of catalyst fines increases the refiner's catalyst costs, and are environmentally undesirable.

The feedstock, that is, the hydrocarbons to be cracked, may include in whole or in part, a gas oil (e.g., light, medium, or heavy gas oil) having an initial boiling point above about 204° C., a 50% point of at least about 260° C., and an end point of at least about 315° C. The feedstock may also include deep cut gas oil, vacuum gas oil, thermal oil, residual oil, cycle stock, whole top crude, tar sand oil, shale oil, synthetic fuel, heavy hydrocarbon fractions derived from the destructive hydrogenation of coal, tar, pitches, asphalts, hydrotreated feedstocks derived from any of the foregoing, and the like. As will be recognized, the distillation of higher boiling petroleum fractions above about 400° C. must be carried out under vacuum in order to avoid thermal cracking. The boiling temperatures utilized herein are expressed in terms of convenience of the boiling point corrected to atmospheric pressure. Resids or deeper cut gas oils having an end point of up to about 700° C., even with high metals contents, can also be cracked using the invention.

It is conventional to use an additive catalyst with different properties along with a conventional catalyst to form an optional mixed catalyst system. The catalyst composition of this invention may be combined with other large-pore zeolites, e.g., zeolites X, Y, ultrastable Y (USY), rare earth exchanged Y (REY), and rare earth exchanged ultrastable Y (RE-USY) among others. The catalyst composition of this invention may also be combined with shape-selective zeolites, e.g., zeolites ZSM-5, ZSM-11, ZSM-12, and ZSM-22, among others.

The large-pore molecular sieve component may comprise from about 5 to about 60 weight percent of the catalyst composition. The additive catalyst component may comprise from about 0.5 to about 50, for example, from about 2 to about 50, weight percent of the catalyst composition.

Although neither the cracking catalyst nor the additive catalyst need be steamed prior to use in the present process, and, in fact, are typically not steamed prior to use herein, they may be steamed at a temperature of from about 300° C. to about 800° C. for a time of from about 1 to about 200 hours in about 5 to about 100% steam.

EXAMPLES

The following examples are presented to illustrate the invention.

Catalysts of this invention and comparative catalysts were prepared and tested for attrition resistance as represented by an Attrition Index (AI). The Attrition Index is defined as the weight percentage of the fines generated during the test that are 20 microns or less in size relative to the amount of material larger than 20 microns present before the test. In the test, a 7 cc catalyst sample is contacted in a 1 inch (inside diameter) U-tube with an air jet formed by humidified (60%) air through an 0.07 inch nozzle at 21 liters per minute for one hour.

$$AI = 100 * \frac{\text{wt. \% fines } AA - \text{wt. \% fines } BA}{100 - \text{wt. \% fines } BA}$$

where BA is before attrition test and AA is after attrition test. The lower the Attrition Index, the more attrition resistant is the catalyst.

With the large-pore zeolites ultrastable Y (USY) and mordenite, phosphorus addition according to the method of this invention was not found to increase the resistance to catalyst attrition, however, surprisingly, phosphorus addition according to the method of this invention to catalysts formed from other large-pore zeolites, Beta and ZSM-12, was found to significantly improve the catalyst attrition resistance.

Example 1

A zeolite ultrastable Y type (USY) catalyst was prepared by spray drying an aqueous slurry, which was aged 4 after mixing, containing 11.3 parts by weight (PBW) zeolite USY (Tosoh USA Inc., Atlanta, Ga., Tosoh I. D. HSZ-360HUA, dry basis, unit cell size 24.30 Å); 22.7 PBW Nalco colloidal silica (Nalco Chemical Co., Chicago, Ill., No. 1034A, 34% $SiO_2$); 1.0 PBW of alumina (Condea Chemie GMBH, Hamburg, Germany, Condea Pural SB, 75% solids) peptized with 0.2 PBW formic acid (90%) and 5.4 PBW deionized (DI) water; 14.1 PBW Thiele RC-32 clay slurry (Thiele Kaolin Company, Wrens, Ga., RC-32 clay slurry, 60.37% solids); and 45.3 PBW DI water. The spray dryer (Komline-Sanderson, Peapack, N.J.) was operated at 350° F., and 6 psig air pressure with a 0.04–0.06 inch nozzle at 200 cc/min using a Moyno feed pump (Springfield, Ohio).

The sequence of preparing the catalyst slurry before spray drying was to combine a source of silica (S) and a source of alumina (A), then to add a siliceous crystalline material, e.g., a zeolite, (Z), and finally to add a clay (C). A short-hand representation of the sequence of preparing the catalyst slurry before spray drying is SAZC. The catalyst composition was 40 wt. % zeolite USY, 27.3 wt. % silica, 2.7 wt. % alumina, and 30 wt. % clay. The binder alumina to phosphorus weight ratio was $Al_2O_3/P=\infty$.

After spray drying, the catalyst was calcined at 1,000° F. for 3 hours in air.

Example 2

A zeolite ultrastable Y type (USY) catalyst was prepared by spray drying an aqueous slurry, which was aged 4 hours after mixing, containing 11.0 parts by weight (PBW) zeolite USY (Tosoh grade HSZ-360 HUA, unit cell size 24.30 Å); 22.0 PBW Nalco colloidal silica; 1.0 PBW alumina peptized with 0.1 PBW formic acid (90%) and 5.2 PBW deionized (DI) water; 13.6 PBW Thiele RC-32 clay slurry; 3.2 PBW phosphoric acid (86.1%) and 43.9 PBW DI water.

With the source of phosphorus represented by P, a short-hand representation of the sequence of preparing the catalyst slurry before spray drying is SAZCP. The catalyst composition was 40 wt. % zeolite USY, 27.3 wt. % silica, 2.7 wt. % alumina, and 30 wt. % clay. The binder alumina to phosphorus weight ratio was $Al_2O_3/P=0.84$.

After spray drying, the catalyst was calcined at 1,000° F. for 3 hours in air.

Example 3

A mordenite catalyst was prepared by spray drying an aqueous slurry containing 14.8 parts by weight (PBW) TEA mordenite (synthesized by methods described in U.S. Pat. No. 4,052,472); 29.7 PBW Nalco colloidal silica; 1.3 PBW alumina peptized with 0.2 PBW formic acid (90%) and 7.0 PBW deionized (DI) water; 18.3 PBW Thiele RC-32 clay slurry; and 28.7 PBW DI water.

A short-hand representation of the sequence of preparing the catalyst slurry before spray drying is ZCSA. The catalyst composition was 40 wt. % mordenite, 27.3 wt. % silica, 2.7 wt. % alumina, and 30 wt. % clay. The binder alumina to phosphorus weight ratio was $Al_2O_3/P=\infty$.

After spray drying, the catalyst was calcined at 1,200° F. for 2 hours in air.

Example 4

A mordenite catalyst was prepared by spray drying an aqueous slurry containing 14.6 parts by weight (PBW) of the same TEA mordenite used in Example 3; 26.9 PBW Nalco colloidal silica; 1.2 PBW alumina peptized with 0.1 PBW formic acid (90%) and 6.4 PBW deionized (DI) water; 18.2 PBW Thiele RC-32 clay slurry; 3.4 PBW phosphoric acid (86.1%) and 29.2 PBW of DI water.

A short-hand representation of the sequence of preparing the catalyst slurry before spray drying is SAZCP. The catalyst composition was 41 wt. % mordenite, 25.6 wt. % silica, 2.6 wt. % alumina, and 30.8 wt. % clay. The binder alumina to phosphorus weight ratio was $Al_2O_3/P=1.0$.

After spray drying, the catalyst was calcined at 1,000° F. 2 hours in air.

Table 1 shows the chemical physical properties of catalysts prepared in the above examples. The addition of phosphorus does not significantly improve the attrition resistance for the large-pore zeolite USY based catalyst produced by the method of this invention and decreases the attrition resistance for a large-pore mordenite based catalyst produced by the method of this invention.

TABLE 1

| Example No. | 1 | 2 | 3 | 4 |
|---|---|---|---|---|
| Preparation | | | | |
| Zeolite | USY | USY | Mordenite | Mordenite |
| Sequence | SAZC | SAZCP | ZCSA | SAZCP |
| Zeolite, wt. % | 40 | 40 | 40 | 41 |
| Silica, wt. % | 27.3 | 27.3 | 27.3 | 25.6 |
| Alumina, wt. % | 2.7 | 2.7 | 2.7 | 2.6 |
| Clay, wt. % | 30 | 30 | 30 | 30.8 |
| Binder | | | | |
| $SiO_2/Al_2O_3$ | 10.0 | 10.0 | 10.0 | 10.0 |
| $Al_2O_3/P$ | ∞ | 0.8 | ∞ | 1.0 |
| Phosphorus Source | — | H | — | H |
| H — Phosphoric acid; N — Ammonium Dihydrogen Phosphate | | | | |
| Slurry pH | 3.9 | 2.1 | 4.0 | 1.4 |
| Chemical Analysis | | | | |
| $SiO_2$, wt. % | 75.8 | 71.2 | N.A. | N.A. |
| $Al_2O_3$, wt. % | 18.8 | 17.4 | N.A. | N.A. |
| P, wt. % | 0.0 | 2.7 | 0.0 | 1.9 |
| Na, ppm | 1,310 | 1,010 | N.A. | 1,380 |
| $Al_2O_3/P$, wt. %/wt. % | ∞ | 6.4 | ∞ | N.A. |
| Physical Properties | | | | |
| Pore Volume, cc/gm | 0.54 | 0.60 | N.A. | 0.52 |
| Surface Area, $m^2$/gm | 274 | 230 | N.A. | 188 |
| Attrition Index, calcined | 4 | 3 | 4 | 11 |

Notes: N.A. — Data are not available

Example 5

A zeolite Beta catalyst was prepared by spray drying an aqueous slurry containing 14.3 parts by weight (PBW) zeolite Beta synthesized by methods described in U.S. Pat. No. 3,308,069 (Reissue Pat. No. 28,341); 26.3 PBW Nalco colloidal silica; 1.2 PBW alumina peptized with 0.1 PBW formic acid (90%) and 6.2 PBW deionized (DI) water; 17.8 PBW Thiele RC-32 clay slurry; and 34.1 PBW DI water.

A short-hand representation of the sequence of preparing the catalyst slurry before spray drying is SAZC. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=\infty$.

After spray drying, the catalyst was calcined at 1,000° F. for 3 hours in air.

Example 6

A zeolite Beta catalyst was prepared by spray drying an aqueous slurry containing 11.6 parts by weight (PBW) of the same zeolite Beta used in Example 5; 23.2 PBW Nalco colloidal silica; 1.1 PBW alumina peptized with 0.2 PBW formic acid (90%) and 5.5 PBW deionized (DI) water; 14.3 PBW Thiele RC-32 clay slurry; 3.5 PBW ammonium dihydrogen phosphate (99.0%); and 40.6 PBW DI water.

A short-hand representation of the sequence of preparing the catalyst slurry before spray drying is SCZPA. The catalyst composition was 40 wt. % zeolite Beta, 27.3 wt. % silica, 2.73 wt. % alumina, and 29.97 wt. % clay. The binder alumina to phosphorus weight ratio was $Al_2O_3/P=1.0$.

After spray drying, the catalyst was calcined at 1,000° F. for 3 hours in air.

Example 7

A zeolite ZSM-12 catalyst was prepared by spray drying an aqueous slurry containing 13.3 parts by weight (PBW) zeolite ZSM-12 synthesized by a method described in U.S. Pat. No. 3,970,544; 29.4 PBW Nalco colloidal silica; 16.5 PBW Thiele RC-32 clay slurry; and 40.8 PBW deionized water.

A short-hand representation of the sequence of preparing the catalyst slurry before spray drying is CZS. The catalyst composition was 40 wt. % zeolite ZSM-12, 30 wt. % silica, and 30 wt. % clay. The binder alumina to phosphorus weight ratio was $Al_2O_3/p=0$.

After spray drying, the catalyst was calcined at 1,200° F. for 2 hours in air.

Example 8

A zeolite ZSM-12 catalyst was prepared by spray drying an aqueous slurry containing 13.9 parts by weight (PBW) of the same zeolite ZSM-12 described in Example 7; 34.8 PBW Nalco colloidal silica; 9.6 PBW Kaopaque 10S kaolin clay (Dry Branch Kaolin Company, Dry Branch, Ga., ID: Kaopaque 10S, 86.76% solids); 3.2 PBW ammonium dihydrogen phosphate (99.0%); and 38.5 PBW deionized water.

A short-hand representation of the sequence of preparing the catalyst slurry before spray drying is SCZP. The catalyst composition was 41 wt. % zeolite ZSM-12, 34.8 wt. % silica, and 24.2 wt. % clay. The binder alumina to phosphorus weight ratio was $Al_2O_3/P=0$.

After spray drying, the catalyst was calcined at 1,000° F. for 2 hours in air.

TABLE 2

| Example No. | 5 | 6 | 7 | 8 |
|---|---|---|---|---|
| Preparation | | | | |
| Zeolite | Beta | Beta | ZSM-12 | ZSM-12 |
| Sequence | SAZC | SCZPA | CZS | SCZP |
| Zeolite, wt. % | 41 | 40 | 40 | 41 |
| Silica, wt. % | 25.6 | 27.3 | 30 | 34.8 |
| Alumina, wt. % | 2.6 | 2.7 | — | — |
| Clay, wt. % | 30.8 | 30 | 30 | 24.2 |
| Binder | | | | |
| $SiO_2/Al_2O_3$ | 10.0 | 10.0 | ∞ | ∞ |
| $Al_2O_3/P$ | ∞ | 1.0 | ∞ | 0.0 |
| Phosphorus Source | — | N | — | N |
| H — Phosphoric acid; N — Ammonium Dihydrogen Phosphate | | | | |
| Slurry pH | 3.7 | 3.9 | 3.5 | 4.7 |
| Chemical Analysis | | | | |
| $SiO_2$, wt. % | 78.8 | 73.6 | N.A. | 81.4 |
| $Al_2O_3$, wt. % | 16.2 | 15.8 | N.A. | 10.0 |
| P, wt. % | 0.0 | 2.7 | 0.0 | 1.2 |
| Na, ppm | 1,330 | 905 | 2,500 | 1,220 |
| $Al_2O_3/P$, wt. %/wt. % | ∞ | 5.9 | ∞ | 0.0 |
| Physical Properties | | | | |
| Pore Volume, cc/gm | N.A. | 0.81 | N.A. | 0.44 |
| Surface Area, m²/gm | 322 | 229 | 184 | 56 |
| Attrition Index, calcined | 18 | 3 | 58 | 3 |

Notes: N.A. — Data are not available

Table 2 shows the unexpected improvement in attrition resistance associated with the addition of phosphorus to a catalyst based upon the large-pore zeolites Beta and ZSM-12. The catalysts made in Examples 6 and 8 are catalysts of this invention. The short-hand representations for the mixing sequences of these examples are SCZPA and SCZP.

Surprisingly, even for catalysts containing added phosphorus, variations in the sequence of addition of the components into the mixture to produce the catalyst significantly change the attrition resistance of the resulting catalysts. Also surprisingly, the elimination of added alumina from the mixture to produce the large-pore zeolite based catalyst does not significantly reduce the resistance of the resulting catalysts. The following examples demonstrate these additional novel features of this invention.

Example 9

A zeolite Beta catalyst was prepared by spray drying an aqueous slurry containing 13.6 parts by weight (PBW) of the same zeolite Beta used in Example 5; 22.8 PBW Nalco colloidal silica; 2.3 PBW alumina peptized with 0.3 PBW formic acid (90%) and 11.3 PBW deionized (DI) water; 11.8 PBW Kaopaque 10S kaolin clay; and 37.9 PBW DI water.

A short-hand representation of the sequence of preparing the catalyst slurry before spray drying was ZCSA. The catalyst composition was 40.9 wt. % zeolite Beta, 23.3 wt. % silica, 5.1 wt. % alumina, and 30.7 wt. % clay. The binder alumina to phosphorus weight ratio was $Al_2O_3/P=\infty$.

After spray drying, the catalyst was calcined at 1,000° F. for 3 hours in air.

Example 10

A zeolite Beta catalyst was prepared by spray drying an aqueous slurry containing 9.4 parts by weight (PBW) of the same zeolite Beta used in Example 5; 17.3 PBW Nalco colloidal silica; 1.6 PBW alumina peptized with 0.2 PBW formic acid (90%) and 7.8 PBW deionized (DI) water; 8.1 PBW Kaopaque 10S kaolin clay; 0.9 PBW phosphoric acid (86.1%); and 54.7 PBW of DI water.

A short-hand representation of the sequence of preparing the catalyst slurry before spray drying is ZCPSA. The catalyst composition was 40 wt. % zeolite Beta, 25 wt. % silica, 5 wt. % alumina, and 30 wt. % clay. The binder alumina to phosphorus weight ratio was $Al_2O_3/P=5$.

After spray drying, the catalyst was calcined at 1,000° F. for 3 hours in air.

Example 11

A zeolite Beta catalyst was prepared by spray drying an aqueous slurry containing 11.6 PBW of the same zeolite Beta used in Example 5; 21.4 PBW Nalco colloidal silica; 1.9 PBW alumina peptized with 0.3 PBW formic acid (90%) and 10.2 PBW deionized (DI) water; 10.1 PBW Kaopaque 10S kaolin clay; 3.5 PBW ammonium dihydrogen phosphate (99.0%) and 41.0 PBW DI water A short-hand representation of the sequence of preparing the catalyst slurry before spray drying is ZSPCA. The catalyst composition was 40 wt. % zeolite Beta, 25 wt. % silica, 5 wt. % alumina, and 30 wt. % clay. The binder alumina to phosphorus weight ratio was $Al_2O_3/P=1.8$.

After spray drying, the catalyst was calcined at 1,000° F. for 3 hours in air.

Example 12

A zeolite Beta catalyst was prepared by spray drying an aqueous slurry containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is ZPCSA. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Table 3 shows the chemical physical properties of catalysts prepared in the above examples. Addition of phosphorus to the mixture used to produce the catalysts from the large-pore zeolites did not produce an improvement in attrition resistance as measured by attrition index (AI) for these zeolite Beta based catalysts.

TABLE 3

| Example No. | 9 | 10 | 11 | 12 |
|---|---|---|---|---|
| Preparation | | | | |
| Zeolite | Beta | Beta | Beta | Beta |
| Sequence | ZCSA | ZCPSA | ZSPCA | ZPCSA |
| Zeolite, wt. % | 40 | 40 | 40 | 41 |
| Silica, wt. % | 23.3 | 25 | 25 | 25.6 |
| Alumina, wt. % | 5.1 | 5 | 5 | 2.6 |
| Clay, wt. % | 30.7 | 30 | 30 | 30.8 |
| Binder | | | | |
| $SiO_2/Al_2O_3$ | 4.6 | 5.0 | 5.0 | 10.0 |
| $Al_2O_3/P$ | ∞ | 5.0 | 1.8 | 1.0 |
| Phosphorus Source | — | H | N | H |

TABLE 3-continued

| Example No. | 9 | 10 | 11 | 12 |
|---|---|---|---|---|
| H — Phosphoric acid; N — Ammonium Dihydrogen Phosphate | | | | |
| Slurry pH | N.A. | 2.3 | 3.9 | 1.5 |
| Chemical Analysis | | | | |
| $SiO_2$, wt. % | N.A. | N.A. | 73.6 | N.A. |
| $Al_2O_3$, wt. % | N.A. | N.A. | 18.2 | N.A. |
| P, wt. % | 0.0 | 0.6 | 2.5 | 1.0 |
| Na, ppm | 1,230 | 1,410 | 1,210 | 1,110 |
| $Al_2O_3/P$, wt. %/wt. % | ∞ | N.A. | 7.3 | N.A. |
| Physical Properties | | | | |
| Pore Volume, cc/gm | 0.79 | 0.85 | 0.59 | N.A. |
| Surface Area, m²/gm | 320 | 316 | 242 | 270 |
| Attrition Index, calcined | 11 | 20 | 26 | 16 |

Notes: N.A. — Data are not available

Example 13

A zeolite Beta catalyst was prepared by spray drying an aqueous slurry containing 13.8 parts by weight (PBW) of the same zeolite Beta used in Example 5; 25.5 PBW Nalco colloidal silica; 1.2 PBW alumina peptized with 0.1 PBW phosphoric acid (86.1%) and 6.0 PBW deionized (DI) water; 17.2 PBW Thiele RC-32 clay slurry; 3.1 PBW phosphoric acid (86.1%); and 33.1 PBW DI water.

A short-hand representation of the sequence of preparing the catalyst slurry before spray drying is APZSC. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Example 14

A zeolite Beta catalyst was prepared by spray drying an aqueous slurry containing 11.6 parts by weight (PBW) of the same zeolite Beta used in Example 5; 21.4 PBW Nalco colloidal silica; 1.9 PBW alumina peptized with 0.3 PBW formic acid (90%) and 10.2 PBW deionized (DI) water; 10.0 PBW Kaopaque 10S kaolin clay; 3.4 PBW phosphoric acid (86.1%) and 41.2 PBW DI water.

A short-hand representation of the sequence of preparing the catalyst slurry before spray drying is CPZSA. The catalyst composition was 40 wt. % zeolite Beta, 25 wt. % silica, 5 wt. % alumina, and 30 wt. % clay. The binder alumina to phosphorus weight ratio was $Al_2O_3/P=1.6$.

After spray drying, the catalyst was calcined at 1,000° F. for 3 hours in air.

Example 15

A zeolite Beta catalyst was prepared by spray drying an aqueous slurry containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is SAZCP. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Example 16

A zeolite Beta catalyst was prepared by spray drying an aqueous slurry containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is SAZPC. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Example 17

A zeolite Beta catalyst was prepared by spray drying an aqueous slurry containing 13.2 parts by weight (PBW) of the same zeolite Beta used in Example 5; 26.5 PBW Nalco colloidal silica; 1.2 PBW alumina peptized with 0.2 PBW formic acid (90%) and 6.3 PBW deionized (DI) water; 2.1 PBW Thiele RC-32 clay slurry; 3.9 PBW phosphoric acid (86.1%) and 46.6 PBW DI water.

A short-hand representation of the sequence of preparing the catalyst slurry before spray drying is SAZCP. The catalyst composition was 40 wt. % zeolite Beta, 27.3 wt. % silica, 2.73 wt. % alumina, and 29.97 wt. % clay. The binder alumina to phosphorus weight ratio was $Al_2O_3/P=0.85$.

After spray drying, the catalyst was calcined at 1,000° F. for 3 hours in air.

Example 18

A zeolite Beta catalyst was prepared by spray drying an aqueous slurry containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is SAPZC. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Example 19

A zeolite Beta catalyst was prepared by spray drying an aqueous slurry containing 11.2 parts by weight (PBW) of the same zeolite Beta used in Example 5; 20.5 PBW Nalco colloidal silica; 1.9 PBW alumina peptized with 0.3 PBW formic acid (90%) and 9.8 PBW deionized (DI) water; 13.8 PBW Thiele RC-32 clay slurry; 6.7 PBW phosphoric acid (86.1%) and 35.8 PBW DI water.

A short-hand representation of the sequence of preparing the catalyst slurry before spray drying is SAZCP. The catalyst composition was 40 wt. % zeolite Beta, 25 wt. % silica, 5 wt. % alumina, and 30 wt. % clay. The binder alumina to phosphorus weight ratio was $Al_2O_3/P=0.76$.

After spray drying, the catalyst was calcined at 1,000° F. for 3 hours in air.

Example 20

A zeolite Beta catalyst was prepared by spray drying an aqueous slurry containing 11.2 parts by weight (PBW) of the same zeolite Beta used in Example 5; 20.5 PBW Nalco colloidal silica; 1.9 PBW alumina peptized with 0.3 PBW formic acid (90%) and 9.8 PBW deionized (DI) water; 13.8 PBW Thiele RC-32 clay slurry; 6.7 PBW ammonium dihydrogen phosphate (99.0%); and 35.8 PBW DI water.

A short-hand representation of the sequence of preparing the catalyst slurry before spray drying is SAZCP. The catalyst composition was 40 wt. % zeolite Beta, 25 wt. % silica, 5 wt. % alumina, and 30 wt. % clay. The binder alumina to phosphorus weight ratio was $Al_2O_3/P=0.9$.

After spray drying, the catalyst was calcined at 1,000° F. for 3 hours in air.

TABLE 4

| Example No. | 13 | 14 | 15 | 16 |
|---|---|---|---|---|
| Preparation | | | | |
| Zeolite | Beta | Beta | Beta | Beta |
| Sequence | APZSC | CPZSA | SAZCP | SAZPC |
| Zeolite, wt. % | 41 | 40 | 41 | 41 |
| Silica, wt. % | 25.6 | 25 | 25.6 | 25.6 |
| Alumina, wt. % | 2.6 | 5 | 2.6 | 2.6 |
| Clay, wt. % | 30.8 | 30 | 30.8 | 30.8 |
| Binder | | | | |
| $SiO_2/Al_2O_3$ | 10.0 | 5.0 | 10.0 | 10.0 |
| $Al_2O_3/P$ | 1.0 | 1.6 | 1.0 | 1.0 |
| Phosphorus Source | H | H | H | H |
| H — Phosphoric acid; N — Ammonium Dihydrogen Phosphate | | | | |
| Slurry pH | 1.7 | 2.2 | 1.3 | 1.5 |
| Chemical Analysis | | | | |
| $SiO_2$, wt. % | N.A. | 72.8 | N.A. | N.A. |
| $Al_2O_3$, wt. % | N.A. | 18.6 | N.A. | N.A. |
| P, wt. % | 2.3 | 2.3 | 2.0 | 1.6 |
| Na, ppm | N.A. | 1,230 | 1,160 | 1,080 |
| $Al_2O_3/P$, wt. %/wt. % | N.A. | 8.1 | N.A. | N.A. |
| Physical Properties | | | | |
| Pore Volume, cc/gm | 0.75 | 0.60 | 0.88 | 0.76 |
| Surface Area, m²/gm | 261 | 253 | 274 | 270 |
| Attrition Index, calcined | 10 | 8 | 7 | 6 |

Notes: N.A. — Data are not available

TABLE 5

| Example No. | 17 | 6 | 18 | 19 | 20 |
|---|---|---|---|---|---|
| Preparation | | | | | |
| Zeolite | Beta | Beta | Beta | Beta | Beta |
| Sequence | SAZCP | SCZPA | SAPZC | SAZCP | SAZCP |
| Zeolite, wt. % | 40 | 40 | 41 | 40 | 40 |
| Silica, wt. % | 27.3 | 27.3 | 25.6 | 25 | 25 |
| Alumina, wt. % | 2.7 | 2.7 | 2.6 | 5 | 5 |
| Clay, wt. % | 30 | 30 | 30.8 | 30 | 30 |

TABLE 5-continued

| Example No. | 17 | 6 | 18 | 19 | 20 |
|---|---|---|---|---|---|
| Binder | | | | | |
| $SiO_2/Al_2O_3$ | 10.0 | 10.0 | 10.0 | 5.0 | 5.0 |
| $Al_2O_3/P$ | 0.8 | 0.8 | 1.0 | 0.8 | 0.9 |
| Phosphorus Source | H | N | H | H | N |
| H — Phosphoric acid; N — Ammonium Dihydrogen Phosphate | | | | | |
| Slurry pH | 1.2 | 3.9 | 1.6 | 1.0 | 3.8 |
| Chemical Analysis | | | | | |
| $SiO_2$, wt. % | 73.2 | 73.6 | N.A. | 68.4 | 69.6 |
| $Al_2O_3$, wt. % | 16.8 | 15.8 | N.A. | 16.8 | 16.8 |
| P, wt. % | 2.0 | 2.7 | 2.3 | 2.0 | 3.8 |
| Na, ppm | 1,050 | 905 | N.A. | 750 | 900 |
| $Al_2O_3/P$, wt. %/wt. % | 8.4 | 5.9 | N.A. | 3.3 | 4.4 |
| Physical Properties | | | | | |
| Pore Volume, cc/gm | 0.51 | 0.81 | 0.72 | 0.47 | 0.68 |
| Surface Area, $m^2$/gm | 234 | 229 | 263 | 181 | 205 |
| Attrition Index, calcined | 3 | 3 | 3 | 1 | 1 |

Notes: N.A. — Data are not available

Tables 4 and 5 show the unexpected improvement in attrition index (AI) due to variations in the sequence of component addition to the mixture used to prepare the large-pore zeolite Beta based catalysts. All catalysts prepared by the methods of Example 6 and Examples 13 through 20 are catalysts of this invention. The short-hand representations for the mixing sequences of these examples are APZSC, CPZSA, SAZCP, SAZPC, SCZPA, and SAPZC. Of course, the order of combining the first two components is not important, e.g., SAZPC is equivalent to ASZCP.

The integrity of the catalyst (i.e., attrition resistance) is improved when the binder alumina/phosphorus weight ratio is less than about 5 and preferably less than about 2. Also, the binder alumina/phosphorus weight ratio in the calcined catalyst product should be less than about 10. Since some phosphorus is lost during calcination due to sublimation of volatile phosphorus species, the calcined alumina/phosphorus weight ratio is higher than the binder alumina/phosphorus weight ratio. "Binder alumina" is alumina from sources other than the siliceous crystalline material, e.g., zeolite Beta. Further, the binder silica/alumina ratio should be greater than about 5. "Binder silica" is silica from sources other than the siliceous crystalline material, e.g., zeolite Beta. Generally, the pH of the mixture before spray drying should be greater than or equal to about 1 and less than about 5, specifically greater than or equal to about 1.5 and less than about 4, more specifically greater than or equal to about 2 and less than about 3.

Table 5 also shows that variations in the source of phosphorus and variations in mixture pH have no effect upon the attrition index for the catalyst. The catalysts of Examples 19 and 20 were prepared in a similar fashion, with Example 19 using phosphoric acid and with Example 20 using ammonium dihydrogen phosphate as the source of phosphorus. The catalysts of Examples 19 and 20 have similar attrition indices. The catalysts of Examples 17 and 6, which were prepared using proportions of components which were similar to each other, but different sources of phosphorus, also have similar attrition indices.

An additional improvement in attrition resistance may be achieved by aging the mixture before spray drying. The following examples demonstrate this further improvement associated with this aspect of the invention.

Example 21

A zeolite Beta catalyst was prepared by spray drying an aqueous slurry, which was aged 4 hours after mixing, containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is ZPCSA. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Example 22

A zeolite Beta catalyst was prepared by spray drying an aqueous slurry, which was aged 4 hours after mixing, containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is SAZCP. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

Example 23

A zeolite Beta catalyst was prepared by spray drying an aqueous slurry, which was aged 4 hours after mixing, containing 13.8 parts by weight (PBW) of the same zeolite Beta used in Example 5; 25.4 PBW Nalco colloidal silica; 1.2 PBW alumina peptized with 0.1 PBW formic acid (90%) and 6.0 PBW deionized (DI) water; 17.2 PBW Thiele RC-32 clay slurry; 3.2 PBW phosphoric acid (86.1%); and 33.1 PBW DI water.

A short-hand representation of the sequence of preparing the catalyst slurry before spray drying is SAZPC. The catalyst composition was 41 wt. % zeolite Beta, 25.6 wt. % silica, 2.56 wt. % alumina, and 30.8 wt. % clay. The binder alumina to phosphorus weight ratio was $Al_2O_3/P=1.0$.

After spray drying, the catalyst was calcined at 1,000° F. for 3 hours in air.

TABLE 6

| Example No. | 12 | 21 | 15 | 22 | 16 | 23 |
|---|---|---|---|---|---|---|
| Preparation | | | | | | |
| Zeolite | Beta | Beta | Beta | Beta | Beta | Beta |
| Sequence | ZP-CSA | ZP-CSA | SA-ZCP | SA-ZCP | SA-ZPC | SA-ZPC |
| Mixture Aged, hrs | — | 4 | — | 4 | — | 4 |
| Zeolite, wt. % | 41 | 41 | 41 | 41 | 41 | 41 |
| Silica, wt. % | 25.6 | 25.6 | 25.6 | 25.6 | 25.6 | 25.6 |
| Alumina, wt. % | 2.6 | 2.6 | 2.6 | 2.6 | 2.6 | 2.6 |
| Clay, wt. % | 30.8 | 30.8 | 30.8 | 30.8 | 30.8 | 30.8 |
| Binder | | | | | | |
| $SiO_2/Al_2O_3$ | 10.0 | 10.0 | 10.0 | 10.0 | 10.0 | 10.0 |
| $Al_2O_3/P$ | 1.0 | 1.0 | 1.0 | 1.0 | 1.0 | 1.0 |
| Phosphorus Source | H | H | H | H | H | H |
| H — Phosphoric acid; N — Ammonium Dihydrogen Phosphate | | | | | | |
| Slurry pH | 1.5 | 2.0 | 1.3 | 1.9 | 1.5 | 2.0 |
| Chemical Analysis | | | | | | |
| $SiO_2$, wt. % | N.A. | N.A. | N.A. | N.A. | N.A. | N.A. |
| $Al_2O_3$, wt. % | N.A. | N.A. | N.A. | N.A. | N.A. | N.A. |
| P, wt. % | 1.0 | 2.3 | 2.0 | 2.1 | 1.6 | 2.2 |
| Na, ppm | 1,110 | N.A. | 1,160 | 1,040 | 1,080 | N.A. |
| $Al_2O_3/P$, wt. %/wt. % | N.A. | N.A. | N.A. | N.A. | N.A. | N.A. |
| Physical Properties | | | | | | |
| Pore Volume, cc/gm | N.A. | 0.89 | 0.88 | 0.79 | 0.76 | 0.72 |
| Surface Area, m²/gm | 270 | 274 | 274 | 274 | 270 | 262 |
| AI, calcined | 16 | 11 | 7 | 5 | 6 | 4 |

Notes: N.A. — Data are not available; AI — Attrition Index

Table 6 shows the improvement in attrition index (AI) associated with aging the mixture before spray drying. The catalyst from Example 12 is compared with the catalyst from Example 21, the catalyst from Example 15 is compared with the catalyst from Example 22, and the catalyst from Example 16 is compared with the catalyst from Example 23. The catalysts of Examples 15, 16, 22 and 23 are catalysts of this invention. The short-hand representation for the mixing sequence of these examples is SAZCP.

Example 24

A zeolite Beta catalyst was prepared by spray drying an aqueous slurry containing 11.6 parts by weight (PBW) of the same zeolite Beta used in Example 5; 29.0 PBW Nalco colloidal silica; 7.9 PBW Kaopaque 10S kaolin clay; 2.6 PBW ammonium dihydrogen phosphate (99.0%); and 48.9 PBW deionized water.

A short-hand representation of the sequence of preparing the catalyst slurry is SCZP. The catalyst composition was 40.9 wt. % zeolite Beta, 34.8 wt. % silica, and 24.3 wt. % clay. The binder alumina to phosphorus weight ratio was $Al_2O_3/P°0$.

After spray drying, the catalyst was calcined at 1,200° F. for 2 hours in air.

Example 25

A zeolite Beta catalyst was prepared by spray drying an aqueous slurry containing 13.2 parts by weight (PBW) of the same zeolite Beta used in Example 5; 29.7 PBW Ludox AS-40 colloidal silica (DuPont, Wilmington, Del., 40% $SiO_2$); 9.1 PBW Kaopaque 10S kaolin clay; 3.0 PBW ammonium dihydrogen phosphate (99.0%); and 45.0 PBW deionized water.

A short-hand representation of the sequence of preparing the catalyst slurry is SCZP. The catalyst composition was 40 wt. % zeolite Beta, 36 wt. % silica, and 24 wt. % clay. The binder alumina to phosphorus weight ratio was $Al_2O_3/P=0$.

After spray drying, the catalyst was calcined at 1,000° F. for 2 hours in air.

Example 26

A zeolite Beta catalyst was prepared by spray drying an aqueous slurry containing 12.0 parts by weight (PBW) of the same zeolite Beta used in Example 5; 22.1 PBW Nalco colloidal silica; 11.4 PBW Kaopaque 10S kaolin clay; 2.8 PBW ammonium dihydrogen phosphate (99.0%); and 51.7 PBW deionized water. A short-hand representation of the sequence of preparing the catalyst slurry before spray drying is SCZP. The catalyst composition was 40.9 wt. % zeolite Beta, 25.6 wt. % silica, and 33.5 wt. % clay. The binder alumina to phosphorus weight ratio was $Al_2O_3/P=0$.

After spray drying, the catalyst was calcined at 1,200° F. for 2 hours in air.

Example 27

A zeolite Beta catalyst was prepared by spray drying an aqueous slurry containing 11.4 parts by weight (PBW) of the same zeolite Beta used in Example 5; 21.0 PBW Nalco colloidal silica; 15.4 PBW Thiele RC-32 clay slurry; 2.6 PBW ammonium dihydrogen phosphate (99.0%); and 49.6 PBW deionized water A short-hand representation of the sequence of preparing the catalyst slurry is SCZP. The catalyst composition was 41 wt. % zeolite Beta, 25.6 wt. % silica, and 33.4 wt. % clay. The binder alumina to phosphorus weight ratio was $Al_2O_3/P=0$.

After spray drying, the catalyst was calcined at 1,200° F. for 2 hours in air.

Example 28

A zeolite Beta catalyst was prepared by spray drying an aqueous slurry containing 11.4 parts by weight (PBW) of the same zeolite Beta used in Example 5; 20.9 PBW Nalco colloidal silica; 10.8 PBW Kaopaque 10S kaolin clay; 2.6 PBW ammonium dihydrogen phosphate (99.0%); and 54.3 PBW deionized water.

A short-hand representation of the sequence of preparing the catalyst slurry before spray drying is SCZP. The catalyst composition was 40.9 wt. % zeolite Beta, 25.5 wt. % silica, and 33.6 wt. % clay. The binder alumina to phosphorus weight ratio was $Al_2O_3/P=0$.

After spray drying, the catalyst was calcined at 1,200° F. for 2 hours in air.

Catalysts according to this invention may be prepared without added alumina. Examples 24 through 28 demonstrate this method of catalyst preparation. Catalysts prepared according to these examples are catalysts of this invention. The short-hand representation for the mixing sequence of these examples is SCZP. The chemical physical properties of these catalysts are summarized in Table 7. A comparison between the properties of the catalyst prepared in Example 24 with the catalyst prepared in Example 25 shows no significant difference in the attrition index, therefore, the substitution of a different brand of colloidal silica into the mixture has little effect upon this property. Comparisons between the properties of the catalysts prepared in Examples 26, 27 and 28, show no significant difference in the attrition index associated with the substitution of a different brand of clay in the mixture.

TABLE 7

| Example No. | 24 | 25 | 26 | 27 | 28 |
|---|---|---|---|---|---|
| Preparation | | | | | |
| Zeolite | Beta | Beta | Beta | Beta | Beta |
| Sequence | SCZP | SCZP | SCZP | SCZP | SCZP |
| Zeolite, wt. % | 40.9 | 40 | 40.9 | 41 | 40.9 |
| Silica, wt. % | 34.8 | 36 | 25.6 | 25.6 | 25.5 |
| Silica manufacturer | Nalco | Ludox | Nalco | Nalco | Nalco |
| Clay, wt. % | 24.3 | 24 | 33.5 | 33.4 | 33.6 |
| Clay supplier | Kao-paque | Kao-paque | Kao-paque | Thiele | Kao-paque |
| Binder | | | | | |
| $SiO_2/Al_2O_3$ | ∞ | ∞ | ∞ | ∞ | ∞ |
| $Al_2O_3/P$ | 0.0 | 0.0 | 0.0 | 0.0 | 0.0 |
| Phosphorus Source | N | N | N | N | N |
| H — Phosphoric acid; N — Ammonium Dihydrogen Phosphate | | | | | |
| Slurry pH | 3.9 | 4.5 | 4.6 | 4.8 | 4.5 |
| Chemical Analysis | | | | | |
| $SiO_2$, wt. % | 82.8 | 80.4 | 72.1 | 77.6 | 77.4 |
| $Al_2O_3$, wt. % | 11.8 | 11.2 | 14.6 | 15.4 | 15.8 |
| P, wt. % | 1.3 | 2.0 | 2.2 | 1.7 | 1.8 |
| Na, ppm | 1,260 | 3,300 | 1,010 | 1,010 | 1,560 |
| $Al_2O_3/P$, wt. %/wt. % | 0.0 | 0.0 | 0.0 | 0.0 | 0.0 |
| Physical Properties | | | | | |
| Pore Volume, cc/gm | 0.63 | 0.48 | 0.68 | 0.65 | N.A. |
| Surface Area, m²/gm | 250 | N.A. | 245 | 225 | 216 |
| Attrition Index, calcined | 2 | 1 | 1 | 1 | 3 |

Notes: N.A. — Data are not available

Example 29

A control catalyst used in the present study was a rare earth ultrastable Y type zeolite (RE-USY) catalyst removed from a commercial FCC unit following oxidative regeneration.

Example 30

The catalyst of Example 17 was steamed for 10 hours at 1,450° F. and a pressure of 0 psig using 45% steam.

Example 31

The catalyst of Example 30 was blended with the catalyst of Example 29 to the following additive level:

25% Example 30 / 75% Example 29

An evaluation of the physical chemical properties of the catalyst of Example 30 indicated:

| | |
|---|---|
| Phosphorus (Ash free), wt. % | 2.0 |
| Attrition Index (calcined) | 3 |

The catalysts of Example 29 and Example 31 were evaluated in a fixed-fluidized bed (FFB) unit at 960° F., 1.0 minute catalyst contact time using a Sour Heavy Gas Oil (SHGO) with the properties shown in Table 8. A range of conversions was scanned by varying the catalyst/oil ratios. The FFB results (after interpolation at 65 vol. % conversion) are summarized in Table 9.

At a given conversion, a zeolite Beta catalyst prepared according to this invention shows octane enhancement activity when compared with the commercial RE-USY catalyst as indicated by an increased research octane number (RON). The gasoline yield decreases when a zeolite Beta catalyst prepared according to this invention is blended with the commercial RE-USY equilibrium catalyst. The gasoline yield loss is accompanied by increases in the $C_3^=$, $C_4^=$, $iC_4^=$, $iC_5^=$, and $iC_4$ yields for the catalyst containing zeolite Beta. These compounds are valuable potential feeds for alkylation, di-isopropyl ether (DIPE), methyl tert-butyl ether (MTBE), and tertiary amyl methyl ether (TAME) units.

TABLE 8

| Charge Stock Property | Sour Heavy Gas Oil |
|---|---|
| Pour point, °F. | 95 |
| CCR, wt. % | 0.56 |
| Kinematic viscosity, cs @ 40 C. | 104.8 |
| Kinematic viscosity, cs @ 100 C. | 7.95 |
| Aniline point, °F. | 168.5 |
| Bromine number | 6.9 |
| Gravity, API | 20.1 |
| Carbon, wt. % | 85.1 |
| Hydrogen, wt. % | 12.1 |
| Sulfur, wt. % | 2.6 |
| Nitrogen, wt. % | 0.2 |
| Basic nitrogen, ppm | 465 |
| Nickel, ppm | 0.5 |
| Vanadium, ppm | 0.3 |
| Iron, ppm | 1.2 |
| Copper, ppm | <1.1 |
| Sodium, ppm | 0.8 |

TABLE 9

Effect of Zeolite Beta on Catalytic Performance
Yield Shifts Relative to Example 29 at 65 vol. % Conversion

| Example No. | 31 |
|---|---|
| Δ Research Octane Number (RON) | 1.9 |
| Δ $C_5^+$ gasoline, wt. % | (3.3) |
| Δ $C_5^+$ gasoline + alkylate, vol. % | 4.0 |
| Total Light Olefins | |
| Δ $C_3^=$, wt. % | 1.2 |
| Δ $C_4^=$, wt. % | 1.7 |
| Δ $C_5^=$, wt. % | 1.4 |
| Isobutylene/Isoamylene | |
| Δ $iC_4^=$, wt. % | 1.0 |
| Δ $iC_5^=$, wt. % | 1.1 |
| Isobutane | |
| Δ $iC_4$, wt. % | 0.8 |
| Potential Alkylation Feedstock | |
| Δ $C_4^=$ + Δ $C_3^=$ + Δ $iC_4$, wt. % | 3.7 |

While there have been described what are presently believed to be the preferred embodiments of the invention, those skilled in the art will realize that changes and modifications may be made thereto without departing from the spirit of the invention and it is intended to claim all such changes and modifications as fall within the true scope of the invention.

We claim:

1. A method of cracking hydrocarbons comprising contacting said hydrocarbons under catalytic cracking conditions with an attrition resistant catalyst composition prepared by the steps of:

a) forming a slurry by combining a siliceous crystalline material (Z) having the structure of zeolite Beta, zeolite ZSM-12, or zeolite ZSM-20, with a source of phosphorous (P) and at least two compounds selected from a source of silica (S), clay (C), and a source of alumina (A) in a mixer under aqueous conditions, wherein the siliceous crystalline material (Z), the source of silica (S), the clay (C), and the source of alumina (A) are added to the slurry in the mixer in a sequence selected from SCZP, CSZP, SAZCP, ASZCP, SAZPC, ASZPC, SAPZC, ASPZC, CPZSA, PCZSA, SCZPA, CSZPA, APZSC, and PAZSC in a short-hand representation, wherein the siliceous crystalline material, the source of silica, the clay, and the source of alumina are added to the slurry in the sequence and in amounts effective to produce an attrition index of less than or equal to about 10 for the catalyst composition after the catalyst composition has been calcined; and b) spray drying the slurry at a pH less than or equal to about 5.

2. The method according to claim 1, wherein the hydrocarbons are contacted with the attrition resistant catalyst composition and a second molecular sieve catalyst.

3. The method according to claim 2, wherein the second molecular sieve catalyst comprises a large-pore zeolite.

4. The method according to claim 3, wherein the large-pore zeolite is selected from the group consisting of X, Y, ultrastable Y, rare earth exchanged Y, rare earth exchanged ultrastable Y, and combinations thereof.

5. The method according to claim 2, wherein the second molecular sieve comprises a shape selective zeolite.

6. The method according to claim 5, wherein the shape selective zeolite is selected from the group consisting of ZSM-5, ZSM-11, ZSM-12, ZSM-22, and combinations thereof.

7. The method according to claim 1, wherein the siliceous crystalline material, the source of silica, the clay, and the source of alumina are mixed in amounts effective to make the weight ratio of alumina from sources other than the siliceous crystalline material to phosphorus less than about 5 in the slurry and less than about 10 in the calcined catalyst, while the weight ratio of silica form sources other than the siliceous crystalline material to alumina from sources other than the siliceous crystalline material is greater than or equal to about 5 in the slurry.

8. The method according to claim 1, wherein the siliceous crystalline material, the source of silica, the clay, and the source of alumina are added to the slurry in the sequence and in amounts effective to produce the attrition index of less than or equal to about 7 for the catalyst composition after the catalyst composition has been calcined, and wherein the source of phosphorus is selected from the group consisting of ammonium monohydrogen phosphate, ammonium dihydrogen phosphate, triammonium phosphate, ammonium hypophosphate, ammonium orthophosphate, ammonium dihydrogen orthophosphate, ammonium monohydrogen orthophosphate, ammonium hypophosphite, ammonium dihydrogen orthophosphite, phosphoric acid and mixtures thereof.

9. The method according to claim 1, further comprising aging the slurry at least 1 hour before spray drying it.

10. The method according to claim 1, wherein the siliceous crystalline material, the source of silica, the clay, and the source of phosphorus are added to the slurry in the sequence of:

(a) first, forming an aqueous slurry of the source of silica and the clay;

(b) second, adding the siliceous crystalline material to the slurry; and (c) third, adding the source of phosphorus to the slurry.

11. The method according to claim 1, wherein the siliceous crystalline material, the source of silica, the clay, the source of phosphorus, and the source of alumina are added to the slurry in the sequence of:

(a) first, forming an aqueous slurry of the source of silica and the source of alumina;

(b) second, adding the siliceous crystalline material to the slurry;

(c) third, adding the clay to the slurry; and (d) fourth, adding the source of phosphorus to the slurry.

12. The method according to claim 1, wherein the siliceous crystalline material, the source of silica, the clay, the source of phosphorus, and the source of alumina are added to the slurry in the sequence of:

(a) first, forming an aqueous slurry of the source of silica and the source of alumina;

(b) second, adding the siliceous crystalline material to the slurry;

(c) third, adding the source of phosphorus to the slurry; and (d) fourth, adding the clay to the slurry.

13. The method according to claim 1, wherein the siliceous crystalline material, the source of silica, the clay, the source of phosphorus, and the source of alumina are added to the slurry in the sequence of:

(a) first, forming an aqueous slurry of the source of silica and the source of alumina;

(b) second, adding the source of phosphorus to the slurry;

(c) third, adding the siliceous crystalline material to the slurry; and (d) fourth, adding the clay to the slurry.

14. The method according to claim 1, wherein the siliceous crystalline material, the source of silica, the clay, the source of phosphorus, and the source of alumina are added to the slurry in the sequence of:

(a) first, forming an aqueous slurry of the clay and the source of phosphorus;

(b) second, adding the siliceous crystalline material to the slurry;

(c) third, adding the source of silica to the slurry; and (d) fourth, adding the source of alumina to the slurry.

15. The method according to claim 1, wherein the siliceous crystalline material, the source of silica, the clay, the source of phosphorus, and the source of alumina are added to the slurry in the sequence of:

(a) first, forming an aqueous slurry of the source of silica and the clay;

(b) second, adding the siliceous crystalline material to the slurry;

(c) third, adding the source of phosphorus to the slurry; and (d) fourth, adding the source of alumina to the slurry.

16. The method according to claim 1, wherein the siliceous crystalline material, the source of silica, the clay, the source of phosphorus, and the source of alumina are added to the slurry in the sequence of:

(a) first, forming an aqueous slurry of the source of alumina and the source of phosphorus;

(b) second, adding the siliceous crystalline material to the slurry;

(c) third, adding the source of silica to the slurry; and (d) fourth, adding the clay to the slurry.

17. The method according to claim 1, wherein the source of phosphorus is selected from the group consisting of phosphoric acid, ammonium dihydrogen phosphate, and combinations thereof; the source of silica is selected from the group consisting of colloidal silica, sodium silicate, polysilic acid, ammonium polysilicate solution, silica sol, silica gel, and mixtures thereof; the clay is selected from the group consisting of kaolin, metakaolin, smectite, and mixtures thereof; the source of alumina is selected from pseudoboehmite, aluminum salts, and mixtures thereof; and the siliceous crystalline material comprises zeolite Beta.

18. The method according to claim 1, wherein the catalytic cracking conditions comprise a riser top temperature of from about 500° C. to about 595° C., a catalyst to oil weight ratio of from about 3 to about 12, and a catalyst residence time of from about 0.5 to about 15 seconds.

* * * * *